United States Patent
Choe et al.

(10) Patent No.: US 10,918,862 B1
(45) Date of Patent: Feb. 16, 2021

(54) METHOD FOR AUTOMATED CLOSED-LOOP NEUROSTIMULATION FOR IMPROVING SLEEP QUALITY

(71) Applicant: HRL Laboratories, LLC, Malibu, CA (US)

(72) Inventors: Jaehoon Choe, Agoura Hills, CA (US); Praveen K. Pilly, West Hills, CA (US); Steven W. Skorheim, Canoga Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 212 days.

(21) Appl. No.: 16/100,184

(22) Filed: Aug. 9, 2018

Related U.S. Application Data (63) Continuation-in-part of application No. 15/947,733, filed on Apr. 6, 2018, now Pat. No. 10,413,724, (Continued)

(51) Int. Cl.
  *A61N 1/36* (2006.01)
  *A61N 1/04* (2006.01)
  *A61B 5/00* (2006.01)

(52) U.S. Cl.
  CPC ....... *A61N 1/36025* (2013.01); *A61N 1/0456* (2013.01); *A61N 1/36031* (2017.08); (Continued)

(58) Field of Classification Search
  CPC ............ A61N 1/36025; A61N 1/36031; A61N 1/025; A61N 1/0456; A61M 21/00; (Continued)

(56) References Cited

U.S. PATENT DOCUMENTS 6,435,876 B1  8/2002  Chen
6,751,505 B1  6/2004  Van Den Honert
(Continued)

FOREIGN PATENT DOCUMENTS

EP    2409641 A1    1/2012
WO    WO 2016-182947 A1    11/2016

OTHER PUBLICATIONS

Merzagora, Anna C., G. Foffani, I. Panyavin, L Mordillo-Mateos, J. Aguilar, Banu Onaral, and A. Oliviero. "Prefrontal hemodynamic changes produced by anodal direct current stimulation." Neuroimage 49, No. 3 (2010): pp. 2304-2310.

(Continued)

*Primary Examiner* — Rex R Holmes
(74) *Attorney, Agent, or Firm* — Tope-McKay & Associates (57) ABSTRACT

Described is a system for adaptable neurostimulation intervention. The system monitors a set of neurophysiological signals in real-time and updates a physiological and behavioral model. The set of neurophysiological signals are classified in real-time based on the physiological and behavioral model. A neurostimulation intervention schedule is generated based on the classified set of neurophysiological signals. The system activates electrodes via a neurostimulation intervention system to cause a timed neurostimulation intervention to be administered based on the neurostimulation intervention schedule. The neurostimulation intervention schedule and timed neurostimulation intervention are refined based on new sets of neurophysiological signals.

21 Claims, 7 Drawing Sheets

Related U.S. Application Data which is a continuation-in-part of application No. 15/332,787, filed on Oct. 24, 2016, now Pat. No. 10,307,592, and a continuation-in-part of application No. 15/583,983, filed on May 1, 2017, now abandoned.

(60) Provisional application No. 62/516,350, filed on Jun. 7, 2017, provisional application No. 62/245,730, filed on Oct. 23, 2015, provisional application No. 62/330,440, filed on May 2, 2016, provisional application No. 62/570,669, filed on Oct. 11, 2017.

(52) U.S. Cl.
CPC ........... *A61B 5/4815* (2013.01); *A61B 5/4818* (2013.01); *A61N 1/36017* (2013.01)

(58) Field of Classification Search
CPC .......... A61M 21/02; A61M 2021/0055; A61M 2205/502; A61M 2205/52; A61M 2230/10; A61M 2021/0072; A61B 5/048; A61B 5/7264; A61B 5/7278; A61B 5/4806; A61B 5/7275; A61B 5/6814; A61B 5/4836; A61B 5/0476; A61B 2560/0223
See application file for complete search history.

(56) References Cited

U.S. PATENT DOCUMENTS

| | | |
|---|---|---|
| 7,153,139 B2 | 12/2006 | Wen et al. |
| 9,149,599 B2 | 10/2015 | Walter |
| 2003/0225340 A1 | 12/2003 | Collura |
| 2006/0041242 A1 | 2/2006 | Stypulkowski |
| 2007/0060974 A1 | 3/2007 | Lozano |
| 2007/0213786 A1 | 9/2007 | Sackellares et al. |
| 2008/0195166 A1* | 8/2008 | Sun ................. A61B 5/4815 607/18 |
| 2011/0118534 A1 | 5/2011 | Baror |
| 2011/0159467 A1 | 6/2011 | Peot |
| 2011/0288610 A1 | 11/2011 | Brocke |
| 2012/0184870 A1 | 7/2012 | Shaw |
| 2013/0011817 A1 | 1/2013 | Cohen Kadosh |
| 2013/0225953 A1 | 8/2013 | Oliviero |
| 2013/0288223 A1 | 10/2013 | Watterson |
| 2013/0338738 A1 | 12/2013 | Garcia Molina |
| 2014/0038147 A1 | 2/2014 | Morrow |
| 2014/0288614 A1 | 5/2014 | Hagedorn |
| 2014/0275926 A1 | 9/2014 | Scott et al. |
| 2015/0050623 A1 | 2/2015 | Falash |
| 2015/0066104 A1 | 3/2015 | Wingeier |
| 2015/0079560 A1 | 3/2015 | Cowan |
| 2015/0105837 A1 | 4/2015 | Aguilar Domingo |
| 2015/0174418 A1 | 6/2015 | Tyler |
| 2015/0238762 A1 | 8/2015 | Pal |
| 2015/0294074 A1 | 10/2015 | Kawato |
| 2016/0206871 A1 | 7/2016 | Weisend |
| 2016/0256691 A1 | 9/2016 | Cecchi |
| 2017/0043167 A1 | 2/2017 | Widge |
| 2017/0249853 A1 | 8/2017 | Weiss |
| 2017/0304623 A1 | 10/2017 | Tandon |
| 2018/0169411 A1 | 6/2018 | Goodall |
| 2018/0221644 A1 | 8/2018 | Grill |

OTHER PUBLICATIONS

Christoff, J. A. (2002). Foreign Languages: Human Capital Approach Needed to Correct Staffing and Proficiency Shortfalls. Report to Congressional Requesters, pp. 1-50.

Operation and Maintenance Overview, Fiscal Year 2016 Budget Estimates, Feb. 2015, Office of the Under Secretary of Defense (Comptroller) / Chief Financial Officer, p. 13.

Flöel, A., Rösser, N., Michka, O., Knecht, S., & Breitenstein, C. (2008). Noninvasive brain stimulation improves language learning. Journal of Cognitive Neuroscience, 20(8), pp. 1415-1422.

Fregni, F., Boggio, P. S., Nitsche, M., Bermpohl, F., Antal, A., Feredoes, E., . . . & Pascual-Leone, A. (2005). Anodal transcranial direct current stimulation of prefrontal cortex enhances working memory. Experimental brain research, 166 (1), pp. 23-30.

Acheson, D. J., Hamidi, M., Binder, J. R., & Postle, B. R. (2011). A common neural substrate for language production and verbal working memory. Journal of Cognitive Neuroscience, 23(6), pp. 1358-1367.

Anderson, J. R. (1981). Cognitive skills and their acquisition. Psychology Press. pp. 143-146 and pp. 243-249.

Bates, E., & MacWhinney, B. (1989). Functionalism and the competition model. The crosslinguistic study of sentence processing, 3, pp. 73-112.

Pienemann, M. (2005). An introduction to processability theory. Cross-linguistic aspects of processability theory, 30, pp. 179-199.

Schumann, J. H. (1986). Research on the acculturation model for second language acquisition. Journal of multilingual & multicultural development, 7(5), pp. 379-392.

Marshall L, Helgadóttir H, Mölle M, Born J. Boosting slow oscillations during sleep potentiates memory. Nature. 2006; 444(7119): pp. 610-613.

Rudoy JD, Voss JL, Westerberg CE, Paller KA. Strengthening Individual Memories by Reactivating Them During Sleep. Science. Nov. 20, 2009;326(5956): pp. 1079-1079.

Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.

Rasch BH, Born J, Gais S. Combined blockade of cholinergic receptors shifts the brain from stimulus encoding to memory consolidation. J Cogn Neurosci. May 2006; 18(5): pp. 793-802.

Gais S, Born J. Low acetylcholine during slow-wave sleep is critical for declarative memory consolidation. Proc Natl Acad Sci U S A. Feb. 17, 2004; 101(7): pp. 2140-2144.

Rasch B, Buchel C, Gais S, Born J. Odor cues during slow-wave sleep prompt declarative memory consolidation. Science. 2007; 315(5817): pp. 1426-1429.

Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.

Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.

Brincat SL, Miller EK. Frequency-specific hippocampal-prefrontal interactions during associative learning. Nat Neurosci. Apr. 2015; 18(4): pp. 576-581.

McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.

Ji D, Wilson MA. Coordinated memory replay in the visual cortex and hippocampus during sleep. Nat Neurosci. 2007; 10(1): pp. 100-107.

Kali S, Dayan P. Off-line replay maintains declarative memories in a model of hippocampal-neocortical interactions. Nat Neurosci. 2004; 7(3): pp. 286-294.

Rolls ET. Hippocampo-cortical and cortico-cortical backprojections. Hippocampus. 2000; 10: pp. 380-388.

Creutzfeldt OD, Fromm GH, Kapp H. Influence of transcortical d-c currents on cortical neuronal activity. Exp Neurol. Jun. 1962; 5: pp. 436-452.

Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.

Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.

(56) References Cited

OTHER PUBLICATIONS

Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Mölle, M. (2013). Auditory closed-loop stimulation of the sleep slow oscillation anhances memory. Neuron, 78(3), pp. 545-553.
Krause, B., & Cohen Kadosh, R. (2014). Not all brains are created equal: the relevance of individual differences in responsiveness to transcranial electrical stimulation. Frontiers in systems neuroscience, vol. 8, article 25, pp. 1-12.
Santarnecchi, E., Muller, T., Rossi, S., Sarkar, A., Polizzotto, N. R., Rossi, A., & Kadosh, R. C. (2016). Individual differences and specificity of prefrontal gamma frequency-tACS on fluid intelligence capabilities. Cortex, 75, pp. 33-43.
Bikson, M., Bestmann, S., & Edwards, D. (2013). Neuroscience: transcranial devices are not playthings. Nature, 501(7466), p. 167.
Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), pp. 175-195.
Schultz DM, Webster L, Kosek P, et al. (2012). Sensor-driven position-adaptive spinal cord stimulation for chronic pain. Pain Physician,15: pp. 1-12.
Philip P, Demotes-Mainard J, Bourgeois M, Vincent JD. (1991). Efficiency of transcranial electrostimulation on anxiety and insomnia symptoms during a washout period in depressed patients a double-blind study. Biol Psychiatry. Mar. 1;29(5): pp. 451-456.
Weiss MF. (1973). The treatment of insomnia through the use of electrosleep: an EEG study. J Nerv Ment Dis. Aug; 157(2): pp. 108-120.
Lande RG, Gragnani C. (2013) Efficacy of cranial electric stimulation for the treatment of insomnia: a randomized pilot study. Complement Ther Med.;21(1): pp. 8-13. doi: 10.1016/j.ctim.2012.11.007.
Crenshaw MC, Edinger JD. (1999). Slow-Wave Sleep and Waking Cognitive Performance Among Older Adults With and Without Insomnia Complaints Physiology & Behavior, vol. 66, Issue 3, pp. 485-492.
Tyler WJ, Boasso AM, Mortimore HM, et al. (2015) Transdermal neuromodulation of noradrenergic activity suppresses psychophysiological and biochemical stress responses in humans. Scientific Reports;5:13865, pp. 1-17. doi:10.1038/srep13865.
Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), pp. 206-223.
Ferrucci, R., Mameli, F., Guidi, I., Mrakic-Sposta, S., Vergari, M., Marceglia, S. E E. A., . . . & Priori, A. (2008). Transcranial direct current stimulation improves recognition memory in Alzheimer disease. Neurology, 71(7), pp. 493-498.
Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), pp. 117-128.
Landolt, HP, Dijk, DJ, Achermann, P, Borbély, AA. (1996). Brain Research, 738(2): pp. 205-212.
Caffarel, J, Gibson, GJ, Harrison, JP, Griffiths, CJ, Drinnan, MJ. (2006). Comparison of manual sleep staging with automated neural network-based analysis in clinical practice. Med Biol Eng Comput., 44(1-2): pp. 105-110.
Santostasi, G et al. (2016). Phase-locked loop for precisely timed acoustic stimulation during sleep. J Neurosci Methods, 259: pp. 101-114.
Nordin, M., Åkerstedt, T. & Nordin, S. "Psychometric evaluation and normative data for the Karolinska Sleep Questionnaire," Sleep Biol. Rhythms, Oct. 2013, vol. 11, Issue 4, pp. 216-226.
Li, Z. et al. (2009). Unscented Kalman filter for brain-machine interfaces. Public Library of Science, 4(7): e6243, pp. 1-18.

Dmochowski JP, Datta A, Bikson M, Su Y, Parra LC. Optimized multi-electrode stimulation increases focality and intensity at target. J Neural Eng. 8(4):046011, pp. 1-16, 2011.
Weigenand, A., Mölle, M., Werner, F., Martinetz, T., & Marshall, L. (2016). Timing matters: open-loop stimulation does not improve overnight consolidation of word pairs in humans. European Journal of Neuroscience, 44(6), pp. 2357-2368.
Hoy, K. E., Emonson, M. R., Arnold, S. L., Thomson, R. H., Daskalakis, Z. J., & Fitzgerald, P. B. (2013). Testing the limits: investigating the effect of tDCS dose on working memory enhancement in healthy controls. Neuropsychologia, 51(9), pp. 1777-1784.
Office Action 1 for U.S. Appl. No. 15/332,787, dated Sep. 18, 2018.
Response to Office Action 1 for U.S. Appl. No. 15/332,787, dated Nov. 6, 2018.
Notification of Transmittal of International Search Report and the Written Opinion of the International Searching Authority for PCT/US2018/026614; dated Aug. 27, 2018.
International Search Report of the International Searching Authority for PCT/US2018/026614; dated Aug. 27, 2018.
Written Opinion of the International Searching Authority for PCT/US2018/026614; dated Aug. 27, 2018.
Bikson, M., Bestmann, S., & Edwards, D. (2013). Neuroscience: transcranial devices are not playthings. Nature, 501(7466), pp. 167-167.
Choe, J., Coffman, B. A., Bergstedt, D. T., Ziegler, M. D., & Phillips, M. E. (2016). Transcranial direct current stimulation modulates neuronal activity and learning in pilot training. Frontiers in human neuroscience, 10, pp. 1-25.
Schultz DM, Webster L, Kosek P, et al. Sensor-driven position-adaptive spinal cord stimulation for chronic pain. Pain Physician 2012;15: pp. 1-12.
Jacobson, L., Koslowsky, M., & Lavidor, M. (2012). tDCS polarity effects in motor and cognitive domains: a meta-analytical review. Experimental brain research, 216(1), pp. 1-10.
Osorio I, Frei MG, Sunderam S, et al. Automated seizure abatement in humans using electrical stimulation. Ann Neurol 2005;57: pp. 258-268.
Berényi, A., Belluscio, M., Mao, D., & Buzsáki, G. (2012). Closed-loop control of epilepsy by transcranial electrical stimulation. Science, 337(6095), pp. 735-737.
Tergau, F., Naumann, U., Paulus, W., & Steinhoff, B. J. (1999). Low-frequency repetitive transcranial magnetic stimulation improves intractable epilepsy. The Lancet, 353(9171), p. 2209.
Gálvez-Garcia, G., Albayay, J., Rehbein, L., & Tomay, F. (2017). Mitigating Simulator Adaptation Syndrome by means of tactile stimulation. Applied Ergonomics, 58, pp. 13-17.
Ngo, H. V. V., Miedema, A., Faude, I., Martinetz, T., Mölle, M., & Born, J. (2015). Driving Sleep Slow Oscillations by Auditory Closed-Loop Stimulation—A Self-Limiting Process. The Journal of Neuroscience, 35(17), pp. 6630-6638.
Cox, R., Korjoukov, I., de Boer, M., & Talamini, L. M. (2014). Sound asleep: processing and retention of slow oscillation phase-targeted stimuli. PloS one, 9(7), e101567, pp. 1-12.
Santostasi, G., Malkani, R., Riedner, B., Bellesi, M., Tononi, G., Paller, K. A., & Zee, P. C. (2016). Phase-locked loop for precisely timed acoustic stimulation during sleep. Journal of neuroscience methods, 259, pp. 101-114.
Van Elmpt WJ, Nijsen TM, Griep PA, et al. A model of heart rate changes to detect seizures in severe epilepsy. Seizure: 2006;15: pp. 366-375.
Schade CM, Schultz DM, Tamayo N, et al. Automatic adaptation of neurostimulation therapy in response to changes in patient position: results of the Posture Responsive Spinal Cord Stimulation (PRS) Research Study. Pain Physician 2011;14: pp. 407-417.
Little S, Pogosyan A, Neal S, et al. Adaptive deep brain stimulation in advanced Parkinson disease. Ann Neurol 2013;74: pp. 449-457.
Notification of the International Preliminary Report on Patentability Chapter I for PCT/US2018/026614; dated Nov. 14, 2019.
The International Preliminary Report on Patentability Chapter I for PCT/US2018/026614; dated Nov. 14, 2019.
Office Action 1 for U.S. Appl. No. 15/583,983, dated Feb. 12, 2019.

(56) References Cited

OTHER PUBLICATIONS

Apoorvagiri; Mental Stress and its Implications on Reaction time; International Journal of Computer Trends and Technology; May 2013; Mental Stress and its Implications on Reaction time. (Year 2013).
Notice of Allowance for U.S. Appl. No. 15/332,787, dated Jan. 17, 2019.
Office Action 1 for U.S. Appl. No. 15/947,733, dated Feb. 1, 2019.
Response to Office Action 1 for U.S. Appl. No. 15/947,733, dated Apr. 17, 2019.
Notice of Allowance for U.S. Appl. No. 15/947,733, dated May 8, 2019.

* cited by examiner

| Company | System | Features | Advantages | Disadvantages |
|---|---|---|---|---|
| Fisher Wallace | FW Stimulator | Headband with sponge electrodes, Standard stimulation pattern | FDA cleared (not approved), direct cranial stimulation | Stimulation only. No EEG, no feedback loop. Most research is 20+ years old and low impact |
| Alpha-stim | AID | Cranial Electrotherapy Stimulation (earlobe clip), standard wave form stimulation | Easy ear-clip, some supporting studies | No EEG, no feedback loop, supporting evidence is scattered and low impact |
| Thync | Thync Relax Pro | Targets peripheral nerves using TEN | Neck mounted, suppresses parasympathetic nervous system, app for sleep quality tracking | No brain input or stimulation. Needs to be worn when stress occurs. Could interfere with basic survival responses to danger |
| Halo | Halo Sport | Headband with proprietary scalp electrodes, motor cortex stimulation | Direct cranial stimulation, attractive, easy-to-use devices | No product targeting sleep enhancement |

METHOD FOR AUTOMATED CLOSED-LOOP NEUROSTIMULATION FOR IMPROVING SLEEP QUALITY

CROSS-REFERENCE TO RELATED APPLICATIONS

This is a Continuation-in-Part patent application of U.S. application Ser. No. 15/947,733, filed in the United States on Apr. 6, 2018, entitled, "A Method for Low Latency Automated Closed-Loop Synchronization of Neurostimulation Interventions to Neurophysiological Activity," issued as U.S. Pat. No. 10,413,724 on Sep. 17, 2019, which is a Non-Provisional patent application of U.S. Provisional Application No. 62/516,350, filed in the United States on Jun. 7, 2017, entitled, "A Method for Low Latency Automated Closed-Loop Synchronization of Neurostimulation Interventions to Neurophysiological Activity," the entirety of which are hereby incorporated by reference. U.S. application Ser. No. 15/947,733 is a Continuation-in-Part patent application of U.S. application Ser. No. 15/332,787, filed in the United States on Oct. 24, 2016, entitled, "Method and System to Accelerate Consolidation of Specific Memories Using Transcranial Stimulation," issued as U.S. Pat. No. 10,307,592 on Jun. 4, 2019 which is a Non-Provisional patent application of U.S. Provisional Application No. 62/245,730, filed in the United States on Oct. 23, 2015, entitled, "Method and System to Accelerate Consolidation of Specific Memories Using Transcranial Stimulation," the entirety of which are hereby incorporated by reference. U.S. application Ser. No. 15/947,733 is also a Continuation-in-Part patent application of U.S. application Ser. No. 15/583,983, filed in the United States on May 1, 2017, entitled, "System and Method for Neurostimulation-Enhanced Second Language Acquisition," which is a Non-Provisional patent application of U.S. Provisional Application No. 62/330,440, filed in the United States on May 2, 2016, entitled, "A Method for Neurostimulation-Enhanced Second Language Acquisition," the entirety of which are hereby incorporated by reference.

This is ALSO a Non-Provisional Application of U.S. Provisional Application No. 62/570,669, filed in the United States on Oct. 11, 2017, entitled, "A Method for Automated Closed-Loop Neurostimulation for Improving Sleep Quality," the entirety of which is incorporated herein by reference.

GOVERNMENT LICENSE RIGHTS

This invention was made with government support under U.S. Government Contract Number W911NF-16-C-0018. The government has certain rights in the invention.

BACKGROUND OF INVENTION

(1) Field of Invention

The present invention relates to a system for automated neurostimulation intervention and, more particularly, to a system for automated neurostimulation intervention for improving sleep quality.

(2) Description of Related Art

The current landscape of neurostimulation either forgoes individualized and adaptive stimulation to reduce complexity of devices (e.g., bioelectronics by Thync Global, Inc., located at 40 West Main Street, $2^{nd}$ Floor, Los Gatos, Calif. 95030; devices by Halo Neuroscience, located at 735 Market St, Floor 4, San Francisco, Calif. 94103), or achieves fine-grained individualized control of stimulation parameters through the supervision of expert operators or laboratories (see the List of Incorporated Literature References, Literature Reference No. 3). The latter infrastructures, though demonstrably more effective, are unlikely to be available to end users outside of a research setting.

Previous work in neurostimulation for the purposes of sleep quality enhancement have focused on pathologies and disease states that prevent the proper functioning of naturalistic sleep cycles. For example, work by Philip et al. (see Literature Reference No. 6) demonstrated that in a double-blind study, patients given cerebral electro-sleep stimulation showed improvements in anxiety scores and insomnia that otherwise resulted from withdrawal of psychiatric drugs. Similar work has also been performed in cases of insomnia (see Literature Reference Nos. 7 and 8), sleep disruption due to age (see Literature Reference No. 9), and autonomic contribution to sleep quality (see Literature Reference No. 10).

All of these studies have shown significant improvements in sleep quality and behavioral performance measures associated with improved sleep. The above-mentioned devices, while using concepts described in the existing literature, does not take into account the variability of intervention across patient pools. Additionally, the prior literature does not apply interventions in a feedback-based, closed-loop fashion, which can be essential to augmentation of continuous, dynamic processes such as sleep. The current field of study prevents wide application of the sleep-augmentation interventions across diverse populations (such as those in a corporate training pool or consumer cohort), and serve little purpose outside of the small population that responds to the default stimulation settings built in to the devices.

Furthermore, current human neurostimulation devices and methods for sleep enhancement apply stimulation using a set stimulation pattern with a lack of feedback control. This relies on the idea that functional neuroanatomy is common across individuals, which has been demonstrated to be untrue, especially in the context of brain stimulation for therapeutic or cognitive enhancement purposes (see Literature Reference Nos. 1-4).

Another limitation of the current state-of-the-art is the non-targeted nature of interventions; the current field of neurostimulation devices do not monitor neural or physiological signals in real-time and as such, interventions are often made without direct connection to signals of interest. The available literature in the field of neurostimulation-based therapy or performance augmentation show markedly different results when the timing and duration of stimulation are changed, which supports the notion that the temporal component of neurostimulation and the particular stimulation protocol used significantly affects efficacy of the intervention (see Literature Reference Nos. 1 and 5).

Thus, a continuing need exists for a closed-loop sleep improvement system that can be individualized and adaptable to a specific user and does not require the supervision of an expert operator.

SUMMARY OF INVENTION

The present invention relates to a system for automated neurostimulation intervention and, more particularly, to a system for automated neurostimulation intervention for improving sleep quality. The system comprises one or more processors and a non-transitory computer-readable medium having executable instructions encoded thereon such that when executed, the one or more processors perform multiple operations. The system monitors a set of neurophysiological signals in real-time and updates a physiological and behavioral model. The set of neurophysiological signals are classified in real-time based on the physiological and behavioral model. A neurostimulation intervention schedule is generated based on the classified set of neurophysiological signals. The system activates one or more electrodes via a neurostimulation intervention system to cause a timed neurostimulation intervention to be administered based on the neurostimulation intervention schedule. The neurostimulation intervention schedule and timed neurostimulation intervention are continually refined based on new sets of neurophysiological signals.

In another aspect, the system refines the neurostimulation intervention schedule and timed neurostimulation intervention based on behavioral and physiological data.

In another aspect, in generating the neurostimulation intervention schedule, the system generates a profile of a sleep cycle using sleep quality measures and sleep staging data obtained in real-time.

In another aspect, in classifying the set of neurophysiological signals, the system identifies periods of a sleep cycle from the set of neurophysiological signals.

In another aspect, the set of neurophysiological signals are obtained from a plurality of sensors comprising neural sensing sensors and physiological sensing sensors.

In another aspect, in generating the neurostimulation intervention schedule, the system plans the timed neurostimulation intervention using sleep quality measures and sleep staging data.

In another aspect, in causing the timed neurostimulation intervention to be administered, the system causes the timed neurostimulation intervention to be administered in phase with a detected slow-wave neural activity automatically and in closed-loop.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for automated neurostimulation intervention and, more particularly, to a system for automated neurostimulation intervention for improving sleep quality. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Krause, B., & Cohen Kadosh, R. (2014). Not all brains are created equal: the relevance of individual differences in responsiveness to transcranial electrical stimulation. Frontiers in systems neuroscience, vol. 8, article 25, pages 1-12.
2. Santarnecchi, E., Muller, T., Rossi, S., Sarkar, A., Polizzotto, N. R., Rossi, A., & Kadosh, R. C. (2016). Individual differences and specificity of prefrontal gamma frequency-tACS on fluid intelligence capabilities. Cortex, 75, pages 33-43.
3. Bikson, M., Bestmann, S., & Edwards, D. (2013). Neuroscience: transcranial devices are not playthings. Nature, 501(7466), page 167.
4. Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), pages 175-195.
5. Schultz D M, Webster L, Kosek P, et al. (2012). Sensor-driven position-adaptive spinal cord stimulation for chronic pain. Pain Physician, 15: pages 1-12.
6. Philip P, Demotes-Mainard J, Bourgeois M, Vincent J D. (1991). Efficiency of transcranial electrostimulation on anxiety and insomnia symptoms during a washout period in depressed patients a double-blind study. Biol Psychiatry. March 1; 29(5): pages 451-456.
7. Weiss M F. (1973). The treatment of insomnia through the use of electrosleep: an EEG study. J Nery Ment Dis. August; 157(2):108-20.
8. Lande R G, Gragnani C. (2013) Efficacy of cranial electric stimulation for the treatment of insomnia: a randomized pilot study. Complement Ther Med.; 21(1):8-13. doi: 10.1016/j.ctim.2012.11.007.
9. Crenshaw M C, Edinger J D. (1999). Slow-Wave Sleep and Waking Cognitive Performance Among Older Adults With and Without Insomnia Complaints Physiology & Behavior, Volume 66, Issue 3, pages 485-492.
10. Tyler W J, Boasso A M, Mortimore H M, et al. (2015) Transdermal neuromodulation of noradrenergic activity suppresses psychophysiological and biochemical stress responses in humans. Scientific Reports; 5:13865. doi: 10.1038/srep13865.
11. Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), pages 206-223.
12. Ferrucci, R., Mameli, F., Guidi, I., Mrakic-Sposta, S., Vergari, M., Marceglia, S. E. E. A., . . . & Priori, A. (2008). Transcranial direct current stimulation improves recognition memory in Alzheimer disease. Neurology, 71(7), pages 493-498.
13. Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), pages 117-128.
14. Landolt, H P, Dijk, D J, Achermarm, P, Borbely, A A. (19%). Brain Research, 738(2): pages 205-212.
15. Caffarel, J, Gibson, G J, Harrison, J P, Griffiths, C J, Drinnan, M J. (2006). Comparison of manual sleep staging with automated neural network-based analysis in clinical practice. Med Biol Eng Comput., 44(1-2): pages 105-110.
16. Santostasi, G et al. (2016). Phase-locked loop for precisely timed acoustic stimulation during sleep. J Neurosci Methods, 259: pages 101-114.
17. Kecklund, G. and Akerstedt, T. (1992). The Psychometric properties of the Karolinska sleep questionnaire. Journal of Sleep Research, Suppl. 1, page 113.
18. Li, Z. et al. (2009). Unscented Kalman filter for brain-machine interfaces. Public Library of Science, 4(7): e6243.
19. Dmochowski J P, Datta A, Bikson M, Su Y, Parra L C. Optimized multi-electrode stimulation increases focality and intensity at target. J. Neural Eng. 8(4):046011, 2011.
20. Weigenand, A., Mölle, M., Werner, F., Martinetz, T., & Marshall, L. (2016). Timing matters: open-loop stimulation does not improve overnight consolidation of word pairs in humans. European Journal of Neuroscience, 44(6), 2357-2368.
21. Hoy, K. E., Emonson, M. R., Arnold, S. L., Thomson, R. H., Daskalakis, Z. J., & Fitzgerald, P. B. (2013). Testing the limits: investigating the effect of tDCS dose on working memory enhancement in healthy controls. Neuropsychologia, 51(9), 1777-1784.

(2) Principal Aspects

Various embodiments of the invention include three "principal" aspects. The first is a system for automated neurostimulation intervention. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
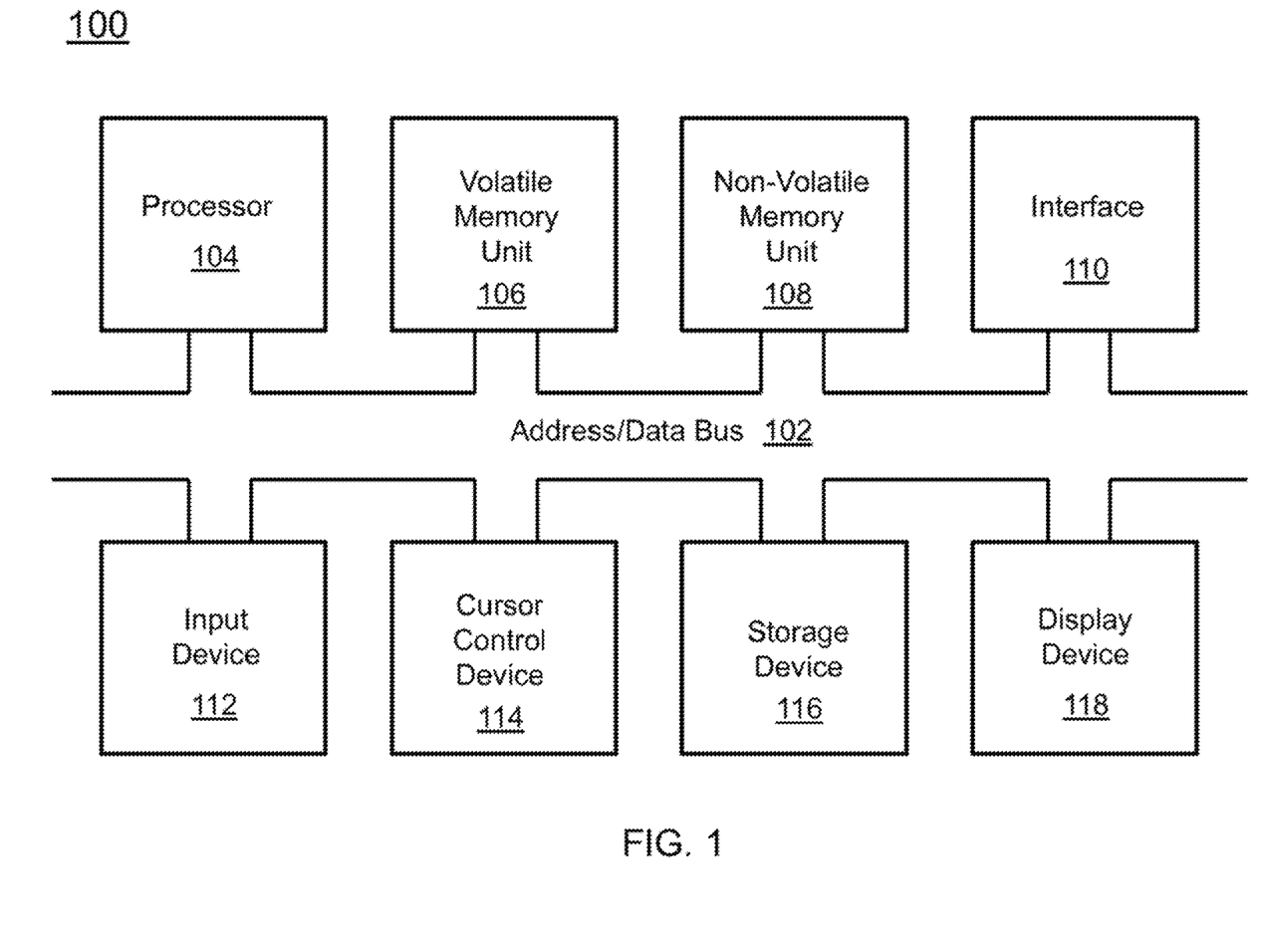
FIG. 1 is a block diagram depicting the components of a system for automated neurostimulation intervention according to some embodiments of the present disclosure.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
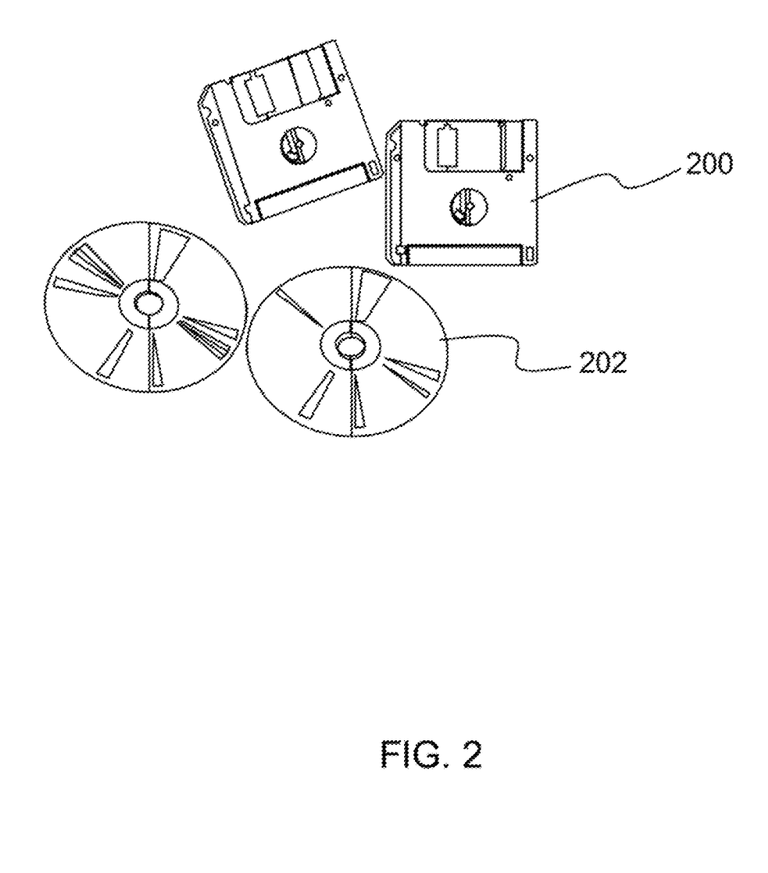
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Figure 3:
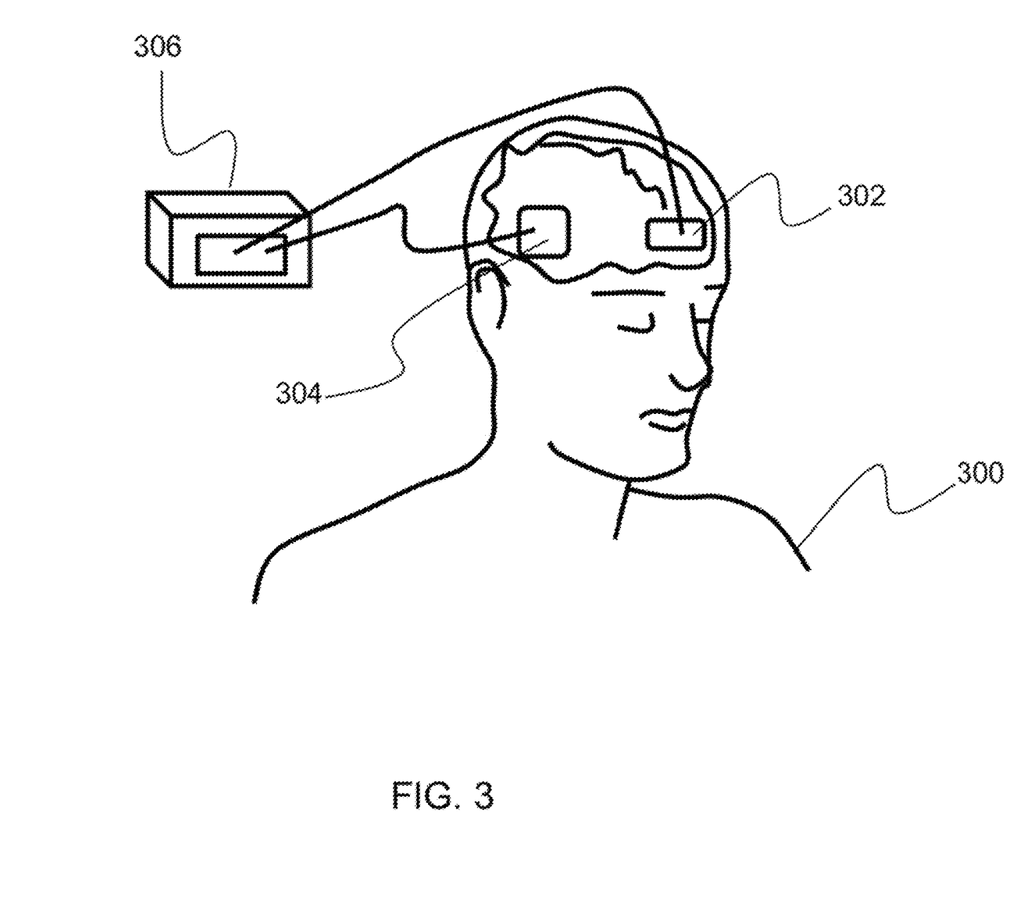
FIG. 3 is an illustration of a human subject receiving neurostimulation via a neural device according to some embodiments of the present disclosure.
Figure 4:
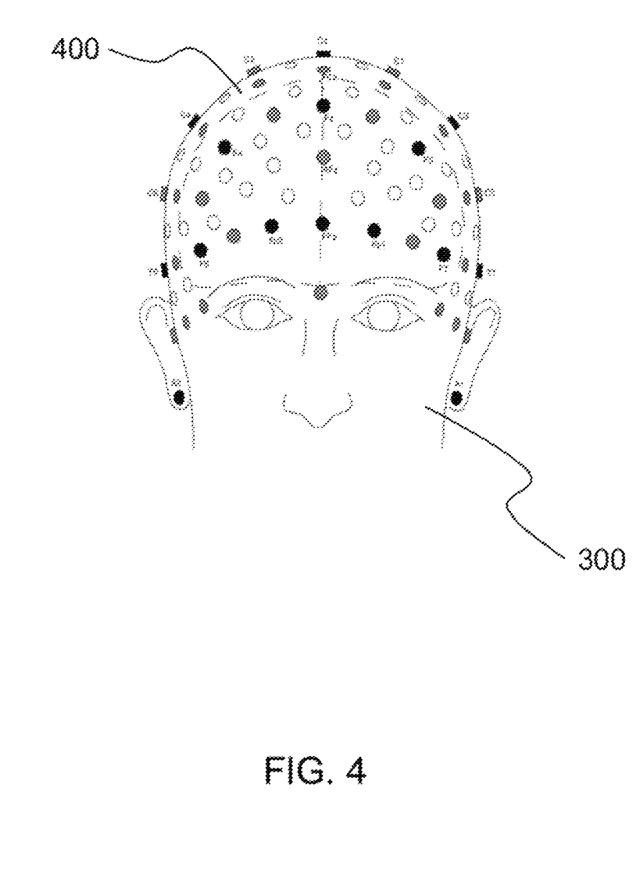
FIG. 4 is an illustration of a human subject wearing a neural cap according to some embodiments of the present disclosure.

Described is a system and method for automatically applying low-latency brain stimulation and obtaining precise timing using neurophysiological signals to trigger and adapt neurostimulation intervention for the purposes of sleep quality enhancement. As depicted in FIG. 3, a human participant 300 is outfitted with neural sensing components 302 and neurostimulation components 304. A device 306 able to generate an electrical current administers neurostimulation through the neurostimulation components 304. The neural sensing components 302 and neurostimulation components 304 can be, for example, part of a neural cap 400 wearable by the human participant 300, as shown in FIG. 4. The neural cap 400 is a neural device comprising one or more electrodes positioned along the scalp for delivering/administering the neurostimulation to the human participant 300. In one embodiment, each electrode is attached to individual wire. As can be appreciated by one skilled in the art, the neural cap 400 may be formed as a net into which electrodes are embedded. The system controls the device 306 to activate the one or more electrodes, causing a timed neurostimulation intervention to be administered.

In another embodiment, a semicircular frame that holds one or more electrodes can surround the user's head. In one arrangement, an anode is placed on each eyelid of the user, and a cathode is applied to the mastoids. In another embodiment, a cranial electrical stimulation (CES) device is used to employ gentle electrical stimulation to the head of the user. The neural device 306 able to generate an electrical current administers neurostimulation by applying a current through one electrode, and it flows through the brain to another electrode (e.g., cathode). The neural device 306 can be a wearable patch that adheres to a portion of the user's head. However, as can be appreciated by one skilled in the art, any suitable neural device 306 can be used provided that it can control stimulation of specific neural regions while performing recordings from the neural device 306 using a targeted arrangement of stimulating electrodes and recording electrodes of the neural device 306.

The human participant 300 receives a personalized, targeted brain stimulation intervention, which is driven through a modeling process in which physiological responses obtained from the neural sensing components 302 and behavioral responses from the human participant 300 are assembled into a physiological and behavioral model 700 system (depicted in FIG. 7 and described below), which acts as a simulacrum of the human participant 300 that yields accurate actions responsive to the detection of specific neurophysiological sleep cues. The physiological and behavioral model 700 described herein ingests data from instruments that monitor heart rate variability (HRV), respiration rate, working memory capacity, reaction time, and current recall performance and uses a set of complex differential equations in order to predict memory retention performance specific to individual users. The physiological forecast is combined with predictions made from analysis of neurological signals which indicate initial performance of device users, which provides an important baseline of activity that contributes to the individualized simulacrum.

Figure 5:
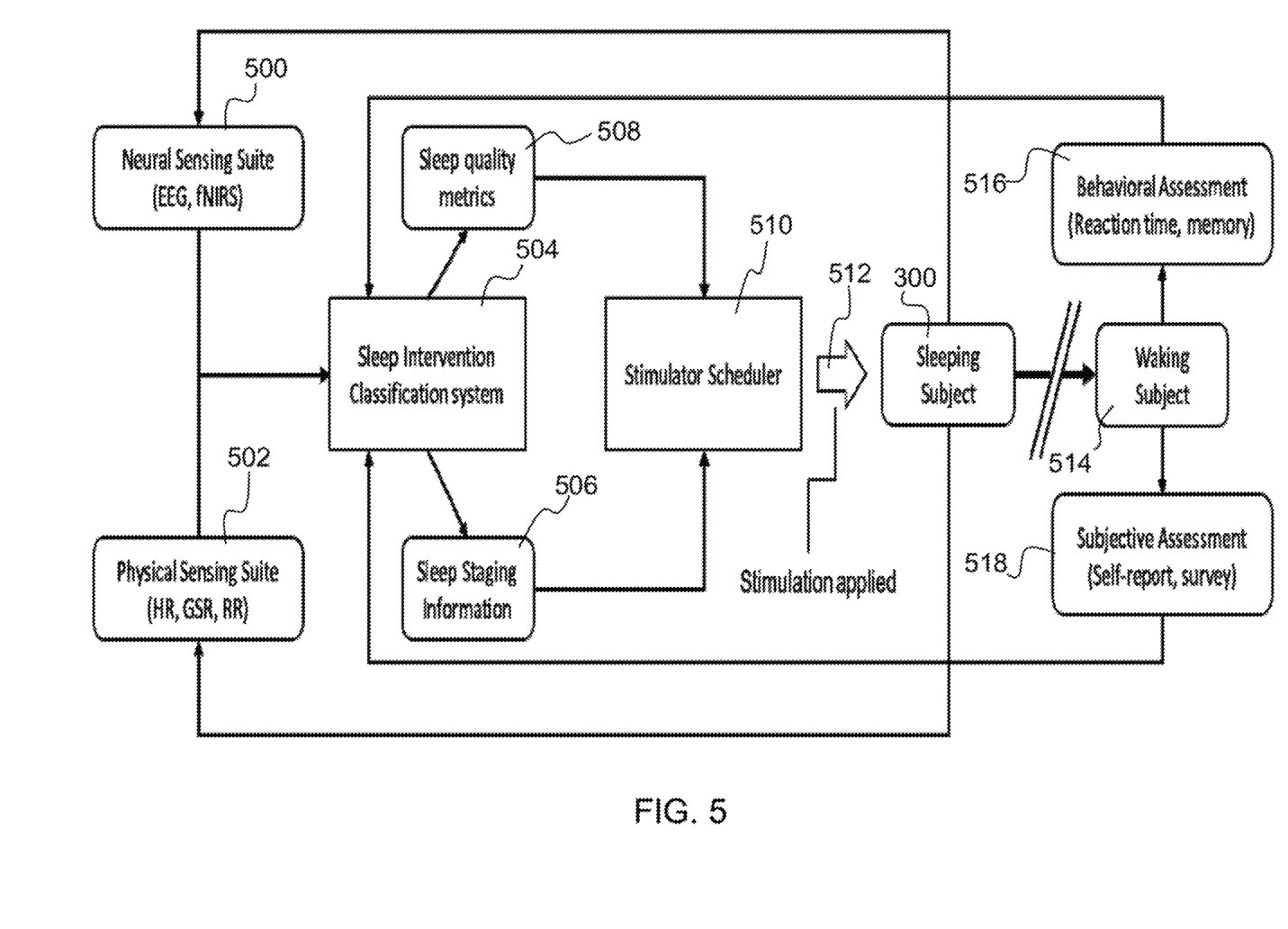
FIG. 5 is an illustration of the architecture of the system for automated neurostimulation intervention according to some embodiments of the present disclosure.

These personalized interventions have been shown to enhance aspects of sleep, sleep-mediated learning, memory-enhancement, and subsequently lead to an increase in overall sleep quality. FIG. 5 depicts the overall system architecture of the invention described herein. A set of sensor-suites, a neural sensing suite 500 and a physical sensing suite 502, monitor the sleeping subject (i.e., human participant 300) in real-time, sending information about the sleep state to the Sleep Intervention Classification system 504. The Sleep Intervention Classification system 504 identifies these complex physiological states through a combination of multi-modal sensing and machine-learning based recognition engines that would be incomprehensible to even an expert human operator. The neural sensing suite 500 includes neural sensors, such as electroencephalogram (EEG) or blood-oxygen-level dependent (BOLD) functional imaging (e.g., near-infrared spectroscopy (fNIRS)). The physiological sensing suite 502 includes non-neural physiological sensors, such as heart rate (HR) sensors (or monitors), electrocardiogram, electromyogram (EMG), electrooculograms (EOG), galvanic skin response (GSR) sensors, rate response (RR) sensors, and other similarly wearable sensors. Muscle tone as measured by electromyogram (EMG) will also be used to determine sleep stage with slow-wave sleep having considerably higher muscle tone than REM sleep. Reduction in eye movements as measured by EOG also indicates slow-wave sleep. Automated classification and analysis of sleep stages (i.e., sleep staging information 506) and self-scoring sleep quality metrics 508 (e.g., restfulness, alertness the following day) further quantifies the improvements to overnight sleep cycles, augmenting the real-time neurophysiological monitoring via the neural sensing suite 500 and the physical sensing suite 502.

The Sleep Intervention Classification system 504 assesses and analyzes the real-time dynamic state of the brain of the sleeping subject 304, and sends this information to the Stimulator Scheduler 510, which then plans the intervention timing to maximize the augmentation of endogenous sleep signals as determined by underlying brain states and personalized user anatomy. The physiological and behavioral model 700 is constructed and used to maximize intervention efficacy (see FIG. 7). An example of endogenous sleep signals are slow-wave oscillations (SWOs), whose presence during sleep has been correlated with improved sleep quality (see Literature Reference No. 14).

Once the intervention is applied (i.e., stimulation applied 512), the neurophysiological data of the sleeping subject/human participant 300 (via the neural sensing suite 500 and the physical sensing suite 502) is again assessed to continually analyze sleep state (element 506) and quality (element 508), which may vary across user populations and may need adjustments based on response signals. Such adjustments are learned, then trained within the classification algorithm, using initial ground truth recordings, then reinforcing those learned signals over time as the feedback signals indicate the overall efficacy of the intervention system. This allows the system to operate in closed-loop and enables autonomous functionality during sleep. This system is further refined through information gained from the waking subject 514 during waking periods, in which behavioral and physiological measures (i.e., behavioral assessment 516 and subjective assessment 518) are integrated into the classification model (i.e., sleep intervention classification system 504) to account for physiological drift and to adapt to changing user sleep patterns. This link also provides a critical, unique link between physiological and behavioral data which has not been used previously in the automatic adaptation of neurostimulative intervention. The data-driven approach according to embodiments of the present disclosure tightly integrates with the software/hardware implementation of the detection and stimulation infrastructure described in U.S. application Ser. No. 15/947,733, which is hereby incorporated by reference as though fully set forth herein. The system described herein can extend and improve sleep, especially in conditions where sleep quality may be compromised due to pathology, environment, or mental state in autonomous fashion following an initial calibration period.

As described above, a sensor suite combining neural and physiological monitoring capabilities is used to monitor the stage and quality of sleep of the human participant 300. In one embodiment, the sensor suite is integrated into an unobtrusive, wearable unit, such as the neural cap 400 shown in FIG. 4, designed to allow users to sleep normally while neurophysiological measurements are recorded and analyzed in real-time. The components of the neural sensing suite 500 may consist of electrophysiological sensors, such as electroencephalogram (EEG), or blood-oxygen-level dependent (BOLD) imaging, such as fNIRS or similar technologies. In the future, miniaturization and optimization of recording technologies may improve to the point in which advanced photo-acoustic imaging paradigms (e.g., PhotoAcoustic Tomography, or PAT), may be used for increased signal quality and subsequent improvements in classification/modeling accuracy. These sensors will be used to detect signals of interest, including, but not limited to, slow-wave oscillations (SWO), sleep spindle activity, sharp wave ripples, and other neurophysiological phenomena that are related to sleep state or quantitative measures of sleep. Thresholds/metrics for these signals will be computed and set per individual user for all of these signals. Non-neural physiological sensors of the physical sensing suite 502 may include heart rate monitors, electrocardiograms, galvanic skin response (GSR) sensors, and other similarly wearable sensors to help correlate subjective sleep quality measures with quantifiable physical metrics. Depending on the task, additional sensing paradigms (e.g., kinematics, electromyograms, and other modalities of physiological sensors) can be used. For instance, body motion sensors can be positioned on the upper and/or lower body of an individual (e.g., arms, legs, torso, back) and used to monitor the kinematics of sleep, such as lying down and changes in sleep position. Electromyograms can be utilized to record the electrical activity of muscles during sleep, such as muscle tone.

Furthermore, kinematics and electromyograms provide quantitative evidence of arousal levels during sleep, a critical metric for automatic sleep staging, and may provide additional insight into task performance for motor-orientated tasks. For example, during a repetitive motor task, the kinematic consistency of an operator may be used as a component of performance that offers insights into the mechanics of human performance. Identification of improvements and decrements to that performance would not be evident when based on purely task-based measures. Such sensor sources are now available in wearable variants that may be worn during nearly any task and during sleep in order to obtain critical biological signals passively while maximizing user comfort. Additional sensor sources, such as these, essentially extend the granularity with which biological signals may be interpreted in order to more accurately assess the effects of stimulation.

Figure 7:
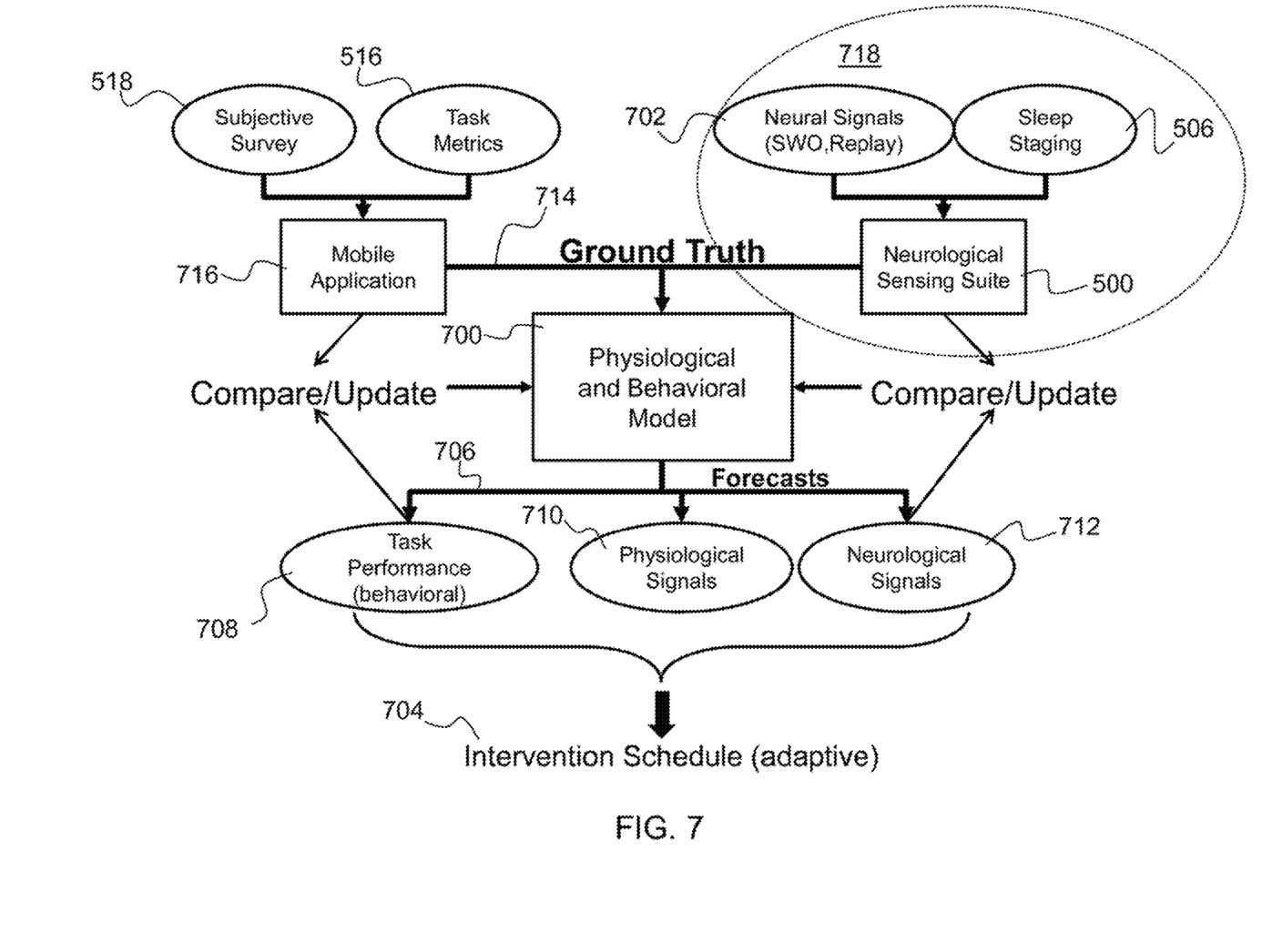
FIG. 7 is an illustration of generation of an intervention schedule according to some embodiments of the present disclosure.

Information obtained from sensors is contained within a physiological and behavioral model 700 depicted in FIG. 7, which monitors behavioral performance (e.g., memory recall accuracy from behavioral assessment/task metrics 516 and subjective assessment/survey 518) and correlates this activity with assessment of neural signals 702 (e.g., the presence of replay-like signals during SWO portions of sleep) and sleep staging 506 during sleep to identify whether the state of the augmented neural activity (e.g., SWO) is having a positive or negative effect on the behavior of interest (e.g., memory recall accuracy). The physiological and behavioral model 700 will then continuously output and adjust the intervention schedule 704 and modulate when to apply the stimulation (e.g., during precise SWO up-state periods) in the correct quantity, dependent on continual forecasts 706 generated by the physiological and behavioral model 700 and updated by data from sensors providing information related to task performance (behavioral) 708, physiological signals 710, and neurological signals 712.

These continuous, real-time measurements will serve to identify periods of the sleep cycle via the sleep intervention classification system 504. This sleep intervention classification system 504 will assemble and analyze the incoming sensor information to generate dynamic state information about the human participant's 300 sleep, with particular emphasis on individual differences in sleeping properties to ensure that generalized models conform to individualized sleep patterns. Initial studies will obtain ground truth signals 714 from users in an initial recording stage, in which baseline indicators of the aforementioned signals are determined, then included into a training set for the classifiers. One non-limiting example of this is the use of known cognitive tests, such as the working memory-based n-back retrieval task, which can be used to challenge a user's working memory capacity in order to define a state of "high cognitive load" and its associated physiological signals 710 and neurological signals 712.

The state information serves to inform the system with overall sleep stage ratios (i.e., amount of time spent in sleep stages 1-4 and REM) and the current sleep stage (i.e., sleep staging information 506). Staging may be done in automated fashion using any of several software techniques available off-the-shelf (see Literature Reference No. 15). Further, the system is also provided with average duration of slow-wave activity (Stage 4 SWO persistence) and sleep spindle events (localized transient signals that occur primarily in Stage 3 sleep) using spectral analysis tools that first identify likely candidates of SW or spindle activity, then identify the likelihood of genuine signal-of-interest presence through comparison with known, stereotypical examples of such signals. These data in combination provide detailed sleep quality metrics 508 specific to a particular human user. This state information will ultimately drive the stimulation scheduler 510 in which neurostimulation interventions (i.e., stimulation applied 512) will be planned in response to changing sleep characteristics. The actual stimulation applied depends highly on the individual stimulated. The frequency of SWO activity may vary a great deal from person to person, so both the frequency of stimulation, as well as the timepoint at which the intervention is applied, is dependent on the observed endogenous SWO of the individual.

Further, there is strong evidence that the intervention must be timed precisely in relation to the natural cycles of SWO activity, wherein stimulation applied out-of-phase results in no effect or even performance decrements (see Literature Reference No. 16). As a result, the system described herein utilizes recorded signals to obtain the phase and frequency of stimulation, then applies the intervention within milliseconds in-phase in order to maximize the efficacy of neurostimulation, in effect planning and executing an intervention schedule 704 to optimize behavioral performance. Previous research has shown that without this closed-loop aspect of stimulation is critical for behavioral improvements, as open-loop style, non-data-driven stimulation fails to induce any memory-based behavioral improvements (see Literature Reference No. 20). Considering the physiological and behavioral model 700 described above, the system described herein also assesses information that define thresholds for overstimulation. Because evidence has recently shown that tES (transcranial electrical stimulation) technologies must occur within an optimal dose envelope, individual limits for stimulation amplitude parameters must be determined (see Literature Reference No. 21), a combined approach of data-driven neurophysiological sensing and behavioral model 700 is used, as described herein, in order to identify whether a human operator is exhibiting "symptoms" of reduced intervention efficacy and accordingly plans future intervention schedules 704 to alleviate under/overstimulation issues.

Moreover, the physiological and behavioral model 700 described above, which forecasts potential behavioral performance, includes information that define thresholds for overstimulation. This allows one to govern the presence of intervention altogether, withholding neurostimulation if the physiological and behavioral model 700 indicates that additional neurostimulation will degrade sleep quality. These systems allow interventions to be planned in such a way that the timing of intervention administration will maximally augment important sub-components of sleep, such as the slow-wave period. Such a system goes beyond the sleep signal identification abilities of human experts, and can identify relevant sleep signals that may have become latent signals due to noise or other aspects of signal acquisition that prevent large-scale, unsupervised sleep staging impossible. The system according to embodiments of the present disclosure enables continual and accurate representations of the user sleep state beyond conventional, human-based methods and, thus, complements and enhances the subjective sleep experience.

In between sleep states, the waking subject 514 may periodically be surveyed to assess behavioral metrics of sleep quality (memory, reaction time) via behavioral assessment 516 and subjective self-assessments 518 of sleep quality (e.g., surveys). In one embodiment, easily replicable memory tasks are administered. For example, a paired-associates test, which determines the extent of memory consolidation that occurred during sleep and is a corollary to the quality of sleep is utilized. Users are presented with a series of paired images, and instructed to memorize each instance as a pair. Following sleep (and sleep-based memory consolidation), users can then be tested in order to determine the accuracy of their recollections by attempting to match single images with their corresponding image as in the originally presented pair. Reaction times are simultaneously collected to determine the speed of recognition.

To avoid reliance on testing/survey procedures that require specialization (e.g., an expert administrator), such subjective assessments 518 and behavioral assessments 516 will be pre-programmed to software that can be used in the human participant's 300 home (e.g., a mobile application 716 in FIG. 7). Non-invasive sensor packages, in the form of portable, wearable devices, will provide quantitative metrics of task behavioral properties. During waking periods, the user can contribute self-perceived sleep quality measures and provide secondary measures of restfulness in order to further refine the physiological and behavioral model 700 and intervention system. A number of possibilities exist for such assessments, but a well-established indicator of subjective sleep quality is the Karolinska Sleep Survey (see Literature Reference No. 17), which is digitized and included in the mobile application.

The combined information from both phases drives this closed-loop, data-driven, feedback system is personalized to the user and can be tuned continually to provide maximal enhancement efficacy over time. This will serve to augment the data collected during sleep and contribute to the accuracy and reliability of the Sleep Intervention Classification System 504 and the models of personalized sleep behaviors contained within. Subjective sleep quality measures are combined with objective measures of sleep in order to generate a richer data profile of an individual's sleep cycle, which includes the physiological and behavioral model 700 described above as well as self-reported sleep quality information. As sleep physiology and subjective perception of restfulness may change over time, it is essential that the sleep-based sensing system and subjective assessments of quality/restfulness be reconciled periodically to adjust and adapt to the changing nature of each night's sleep. To achieve this, the accuracy of the behavioral forecasts 706 produced by the physiological and behavioral model 700 will be monitored to determine the precision of the physiological and behavioral model 700.

An adjustable threshold can then be utilized to trigger a recalibration instance in which the individual may be asked to update a physiological (e.g., re-administration of the respiration rate test) or subjective (re-administration of the Karolinska survey) parameter used by the physiological and behavioral model 700. The neural portion 718 is closed-loop and self-calibrating as described above, so this methodology is unnecessary. The updated parameters may then be incorporated into the physiological and behavioral model 700 identified above, or be included in an additional state-transition layer that continually updates the state of the user; this may be accomplished using a Kalman Filter for user-state updates (see Literature Reference No. 18) or any number of other techniques used to smooth and predict system states based on changing environments/contexts. These update mechanisms ensure that the user models are adapted to the changing brain and behavioral states of the individual.

The stimulation system has been described previously in U.S. application Ser. No. 15/583,983 and U.S. application Ser. No. 15/332,787, which are both hereby incorporated by reference as though fully set forth herein. The stimulation system includes non-invasive stimulation technologies, such as transcranial current stimulation (tCS), transcranial magnetic stimulation (TMS), or ultrasound stimulation (US). Stimulation would ideally be applied over the frontal cortical areas of the brain to augment sleep-related phenomena, such as slow-wave oscillations (SWOs), or temporal-parietal locations similar to that reported in Literature Reference No. 8, which describes "P" sensor locations, which have also been demonstrated to effect positive changes of the SWO and behavioral performance improvements. In addition, placement of electrodes on earlobes is thought to permit microcurrent to travel across the local cranial nerves to the brainstem, thalamus, and cortex. fMRI suggests that cranial electric stimulation (CES) results in cortical deactivation in the midline prefrontal and parietal areas of the brain. Increased spatial coverage may be important for adaptation and stimulation protocol optimization purposes; therefore, stimulation would ideally be configured to be multi-channel capable, particularly with technologies, such as tCS, that benefit from montage-based beam-forming and current targeting techniques (see Literature Reference No. 19) that deliver current to specific sub-regions of the brain using electrical interference tomography (EIT) with arrangements of positive and negative current sources to direct an electrical current field across specific brain regions of interest. This technique allows for highly specific spatial acuity of stimulation (resolution), allowing selective delivery of current to desired brain regions while leaving others unaltered. Additionally, as the understanding of neural mechanisms of interest (e.g., consolidation) are improved, the technique can be used to move the foci of intervention in real-time, allowing for temporally rich stimulation patterns occurring as a sequence of interventions to other brain regions. The primary purpose of EIT is to enhance the flexibility and robustness of stimulation even while adjusting the neuro-stimulative intervention optimized for personalized anatomy or behavioral phenotype.

A key aspect of the invention described herein is the sensing/control system that triggers the onset of stimulation based on salient data about the real-time sleep quality measures, and the ability of the system to maintain gentle electrical stimulation in phase with the natural slow-wave activity of the human brain during sleep. The result is more effective, restful sleep, including cognitive functions associated with sleep (e.g., memory consolidation). Previous research in pilot training and other skill learning programs (see U.S. application Ser. No. 15/583,983 and U.S. application Ser. No. 15/332,787) relied on manual stimulation of trainee pilot subjects without any specificity in time, which reduced the capabilities of the study and reduced the potential for the commercialization of this technology. Many similar efforts in the field of neurostimulation have similar shortcomings, and the possible use case scenarios for neurostimulation are limited when using non-specifically applied interventions. Devices with closed-loop sensing and stimulation capability have been previously disclosed in U.S. application Ser. No. 15/947,733, and the current work can be considered a continuation of that technology.

While components of the invention exist in simplified form, the state-of-the-art currently lacks capacity to personalize stimulation, adapt stimulation for changing environments and applications, and the ability to monitor brain states for maximizing the efficacy of neurostimulative intervention to sleep and learning. Because salient, prototypical implementations of feedback-based closed-loop neuroaugmentative technologies do not currently exist, the capabilities and properties of the technology has been in flux, which has made the conceptualization of complete, turnkey systems exploiting the advantages of the constituent components non-trivial.

Figure 6:
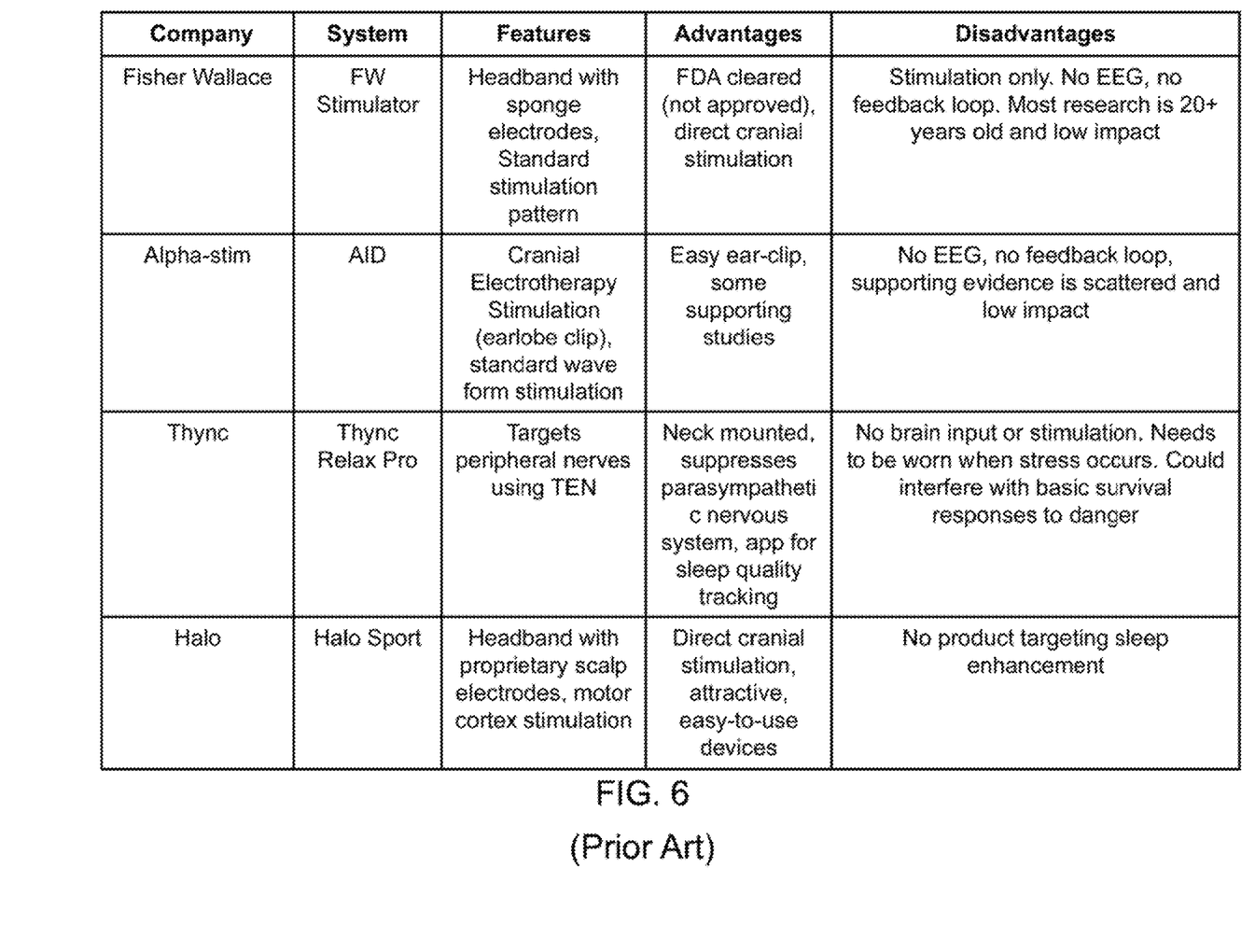
FIG. 6 is a table of currently available products for neurostimulation or sleep enhancement according to prior art.

Further, the utility of the invention described herein is enhanced by the state of the neurotechnology-based appliance market and contemporary research into various implementations of neurostimulative/neuromodulatory devices. The rise of consumer-level neural stimulation devices drives the need for an effective, sophisticated, and unsupervised control system, particularly for those devices aimed at the consumer. The technology described herein substantially improves upon the personalization, efficacy, and specificity of nascent neurostimulative devices. Specifically, the closed-loop brain stimulation system for sleep enhancement substantially improves the efficacy of a variety of products that are currently in use today, including those listed in the table in FIG. 6.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for adaptable neurostimulation, the system comprising:
    one or more processors and a non-transitory memory having instructions encoded thereon such that when the instructions are executed, the one or more processors perform operations of:
        continuous monitoring of a set of neurophysiological signals and a set of task performance metrics of a user in real-time;
        continuously updating a combined physiological and behavioral model with the set of neurophysiological signals and the set of task performance metrics;
        classifying the set of neurophysiological signals in real-time based on the combined physiological and behavioral model;
        generating a neurostimulation intervention schedule based on the classified set of neurophysiological signals;
        activating one or more electrodes via a neurostimulation intervention system to cause a timed neurostimulation intervention to be administered based on the neurostimulation intervention schedule; and
        refining the neurostimulation intervention schedule and timed neurostimulation intervention based on new sets of neurophysiological signals and task performance metrics.

2. The system as set forth in claim 1, wherein the one or more processors further perform operations of refining the neurostimulation intervention schedule and timed neurostimulation intervention based on behavioral and physiological data.

3. The system as set forth in claim 1, where in generating the neurostimulation intervention schedule, the one or more processors further perform an operation of generating a profile of a sleep cycle using sleep quality measures and sleep staging data obtained in real-time.

4. The system as set forth in claim 1, where in classifying the set of neurophysiological signals, the one or more processors further perform an operation of identifying periods of a sleep cycle from the set of neurophysiological signals.

5. The system as set forth in claim 1, wherein the set of neurophysiological signals and the set of task performance metrics are obtained from a plurality of sensors comprising neural sensing sensors and physiological sensing sensors.

6. The system as set forth in claim 1, where in generating the neurostimulation intervention schedule, the one or more processors further perform an operation of planning the timed neurostimulation intervention using sleep quality measures and sleep staging data.

7. The system as set forth in claim 1, where in causing the timed neurostimulation intervention to be administered, the one or more processors further perform an operation of causing the timed neurostimulation intervention to be administered in phase with a detected slow-wave neural activity automatically and in a closed, feedback-based loop.

8. A computer implemented method for adaptable neurostimulation, the method comprising acts of:
    causing one or more processors to execute instructions encoded on a non-transitory computer-readable medium, such that upon execution, the one or more processors perform operations of:
        continuous monitoring of a set of neurophysiological signals and a set of task performance metrics of a user in real-time;
        continuously updating a combined physiological and behavioral model with the set of neurophysiological signals and the set of task performance metrics;
        classifying the set of neurophysiological signals in real-time based on the combined physiological and behavioral model;
        generating a neurostimulation intervention schedule based on the classified set of neurophysiological signals;
        activating one or more electrodes via a neurostimulation intervention system to cause a timed neurostimulation intervention to be administered based on the neurostimulation intervention schedule; and
        refining the neurostimulation intervention schedule and timed neurostimulation intervention based on new sets of neurophysiological signals and task performance metrics.

9. The method as set forth in claim 8, wherein the one or more processors further perform operations of refining the neurostimulation intervention schedule and timed neurostimulation intervention based on behavioral and physiological data.

10. The method as set forth in claim 8, where in generating the neurostimulation intervention schedule, the one or more processors further perform an operation of generating a profile of a sleep cycle using sleep quality measures and sleep staging data obtained in real-time.

11. The method as set forth in claim 8, where in classifying the set of neurophysiological signals, the one or more processors further perform an operation of identifying periods of a sleep cycle from the set of neurophysiological signals.

12. The method as set forth in claim 8, wherein the set of neurophysiological signals and the set of task performance metrics are obtained from a plurality of sensors comprising neural sensing sensors and physiological sensing sensors.

13. The method as set forth in claim 8, where in generating the neurostimulation intervention schedule, the one or more processors further perform an operation of planning the timed neurostimulation intervention using sleep quality measures and sleep staging data.

14. The method as set forth in claim 8, where in causing the timed neurostimulation intervention to be administered, the one or more processors further perform an operation of causing the timed neurostimulation intervention to be administered in phase with a detected slow-wave neural activity automatically and in a closed, feedback-based loop.

15. A computer program product for adaptable neurostimulation, the computer program product comprising:
   computer-readable instructions stored on a non-transitory computer-readable medium that are executable by a computer having one or more processors for causing the processor to perform operations of:
      continuous monitoring of a set of neurophysiological signals and a set of task performance metrics of a user in real-time;
      continuously updating a combined physiological and behavioral model with the set of neurophysiological signals and the set of task performance metrics;
      classifying the set of neurophysiological signals in real-time based on the combined physiological and behavioral model;
      generating a neurostimulation intervention schedule based on the classified set of neurophysiological signals;
      activating one or more electrodes via a neurostimulation intervention system to cause a timed neurostimulation intervention to be administered based on the neurostimulation intervention schedule; and
      refining the neurostimulation intervention schedule and timed neurostimulation intervention based on new sets of neurophysiological signals and task performance metrics.

16. The computer program product as set forth in claim 15, wherein the one or more processors further perform operations of refining the neurostimulation intervention schedule and timed neurostimulation intervention based on behavioral and physiological data.

17. The computer program product as set forth in claim 15, where in generating the neurostimulation intervention schedule, the one or more processors further perform an operation of generating a profile of a sleep cycle using sleep quality measures and sleep staging data obtained in real-time.

18. The computer program product as set forth in claim 15, where in classifying the set of neurophysiological signals, the one or more processors further perform an operation of identifying periods of a sleep cycle from the set of neurophysiological signals.

19. The computer program product as set forth in claim 15, wherein the set of neurophysiological signals and the set of task performance metrics are obtained from a plurality of sensors comprising neural sensing sensors and physiological sensing sensors.

20. The computer program product as set forth in claim 15, where in generating the neurostimulation intervention schedule, the one or more processors further perform an operation of planning the timed neurostimulation intervention using sleep quality measures and sleep staging data.

21. The computer program product as set forth in claim 15, where in causing the timed neurostimulation intervention to be administered, the one or more processors further perform an operation of causing the timed neurostimulation intervention to be administered in phase with a detected slow-wave neural activity automatically and in a closed, feedback-based loop.

\* \* \* \* \*